(12) United States Patent
Cunningham

(10) Patent No.: US 7,074,311 B1
(45) Date of Patent: Jul. 11, 2006

(54) BIOSENSOR ELECTROPHORESIS

(75) Inventor: Brian T. Cunningham, Lexington, MA (US)

(73) Assignee: SRU Biosystems Inc., Woburn, MA (US)

( * ) Notice: Subject to any disclaimer, the term of this patent is extended or adjusted under 35 U.S.C. 154(b) by 393 days.

(21) Appl. No.: 10/431,948

(22) Filed: May 8, 2003

Related U.S. Application Data

(60) Provisional application No. 60/378,691, filed on May 8, 2002.

(51) Int. Cl.
*G01N 27/26* (2006.01)
*G01N 27/453* (2006.01)

(52) U.S. Cl. .................................. 204/450; 204/612

(58) Field of Classification Search ............. 204/450, 204/466, 606, 612, 616; 422/55, 57, 82.05, 422/82.11
See application file for complete search history.

(56) References Cited

U.S. PATENT DOCUMENTS

| | | | |
|---|---|---|---|
| 5,923,031 A * | 7/1999 | Naya ..................... | 250/227.25 |
| 2002/0127565 A1 | 9/2002 | Cunningham et al. ........ | 435/6 |
| 2003/0027327 A1 | 2/2003 | Cunningham et al. ... | 435/287.2 |
| 2003/0027328 A1 | 2/2003 | Cunningham et al. ... | 435/287.2 |

FOREIGN PATENT DOCUMENTS

| | | |
|---|---|---|
| DE | 20108650 U1 * | 8/2001 |
| JP | 200074881 A2 * | 3/2000 |
| WO | WO 02/061429 | 8/2002 |

OTHER PUBLICATIONS

Cowan, J. Opt. Soc. Am. 7(8):1529-1544 (1990).
Magnusson, et al., New Principle for Optical Filters 61(9):1022-1024 (1992).
Pandey, A. and Mann, M., Nature. 405(6788):837-46 (2000).
Patterson, S.D., Current Opinions in Biotechnology, 11(4):413-8 (2000).
Peng, et al., Resonant Scattering for Two-Dimensional Gratings 13(5):993-1005 (1996).
Peng, et al., Experimental Demonstration of Resonant Anomalies in Diffraction from Two-Dimensional Gratings 21(8):549-551 (1996).

* cited by examiner

*Primary Examiner*—Nam Nguyen
*Assistant Examiner*—R. Michelle Vestal
(74) *Attorney, Agent, or Firm*—McDonnell Boehnen Hulbert & Berghoff LLP

(57) ABSTRACT

The invention provides methods of detecting, purifying, quantifying, and separating molecules using an electrophoresis adapted biosensor.

14 Claims, 13 Drawing Sheets

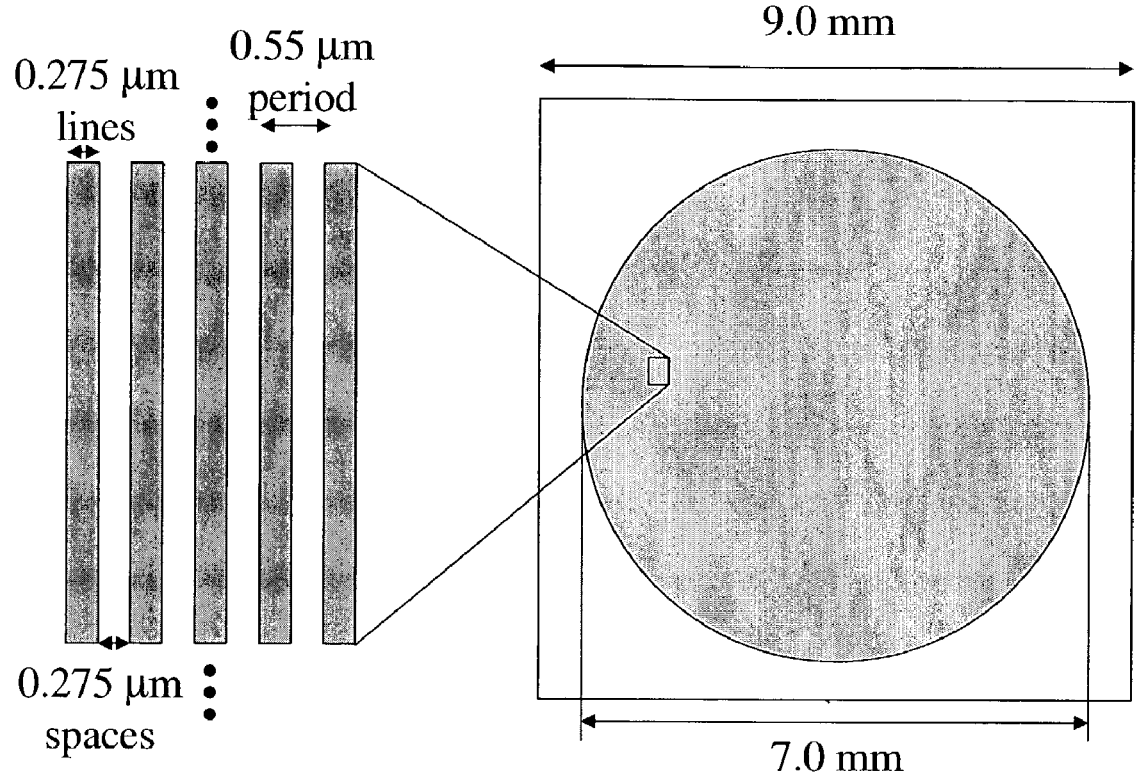
Fig. 2A
Fig. 2B
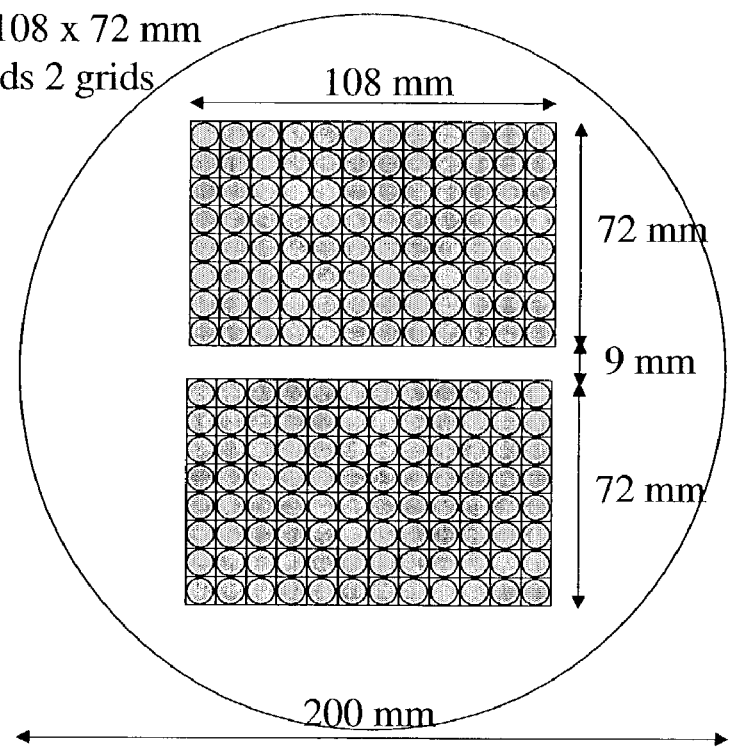
- 1 grid is 108 x 72 mm
- Wafer holds 2 grids
Fig. 2C

Concentric Circle Design

Hexagonal Grid Design

BIOSENSOR ELECTROPHORESIS

PRIORITY

This application claims the benefit of U.S. Provisional Application Ser. No. 60/378,691 filed May 8, 2002.

TECHNICAL AREA OF THE INVENTION

The invention provides compositions and methods for separation, detection, quantification, and purification of molecules.

BACKGROUND OF THE INVENTION

Electrophoresis through agarose or polyacrylamide gels is the standard method used to separate, identify, quantify, and purify nucleic acid fragments. The technique is simple, rapid to perform, and capable of resolving fragments of nucleic acids that cannot be separated adequately by other procedures. Typically, the location of nucleic acids within the gel can be determined by staining with low concentrations of the fluorescent intercalating dye ethidium bromide; bands containing as little as 1–10 ng of nucleic acid can be detected by direct examination of the gel in ultraviolet light. If necessary, these bands of nucleic acids can be recovered from the gel and used for a variety of purposes, including, for example, cloning.

Agarose gels are cast by melting agarose in the presence of a desired buffer until a clear transparent solution is obtained. The melted solution is then poured into a mold and allowed to harden. Upon hardening the agarose forms a matrix. When an electric field is applied across the gel, nucleic acids, which are negatively charged at neutral pH, migrate toward the anode. To obtain maximum resolution of nucleic acid fragments greater than 2 kb in size, agarose gel voltage is typically no more than 5 V/cm. The rate of migration is determined by a number of parameters, including the molecular size of the nucleic acid strands. Larger molecules migrate more slowly because of greater frictional drag and because they work their way through the pores of the gel less efficiently than smaller molecules.

Horizontal slab gels are usually poured onto a glass plate or plastic tray that can be installed on a platform in an electrophoresis tank. The position of stained nucleic acid strands within the gel are measured by photographing the gel while it is illuminated with ultraviolet light. Most typically, the gel image is recorded onto film, although digital imaging systems that are sensitive to light at ~300 nm wavelengths can also be used. Using a long exposure time and a strong UV light source, fluorescence emitted by a little as 1 ng of nucleic acids can be recorded on film.

Polyacrylamide gels are almost always poured between two glass plates that are held apart by spacers (0.5–2.0 mm) and sealed with electrical tape. In this arrangement, most of the acrylamide solution is shielded from exposure to the air, so that inhibition of polymerization by oxygen is confined to a narrow layer at the top of the gel. Polyacrylimide gels have advantages of greater resolving power, greater molecular capacity, and higher purity extraction of recovered nucleic acids compared to agarose gels.

Like nucleic acid electrophoresis, separation of proteins or peptides within a gel can be accomplished by the application of an electrical potential that results in a rate of molecular migration that is dependent on the charge of the molecule, rather than its mass. The electrophoretic mobility of a molecule is equal to the net charge on the molecule divided by its frictional coefficient.

The gel is a loosely cross-linked network that functions to stabilize the protein. For proteins, gels composed of polysaccharide agarose or polyacrylamide are typically used. The percentage of gel used is gauged according to the size of the proteins being separated. For the finest separations, gradient gels are made with a continuous increase in gel percentage along the length of the slab. This approach leads to optimum separation of components in a mixture and the sharpest protein solvent boundaries. At the completion of the run, a dye that stains the proteins is added to the gel to establish the locations of protein bands.

Another electrophoretic method frequently used for characterizing proteins is based on differences in their isoelectric points—called isoelectric focusing. The apparatus consists of a narrow tube containing a gel and a mixture of ampholytes, which are small molecules with positive and negative charges. The ampholytes have a wide range of isoelectric points, and are allowed to distribute in the column under the influence of an electric field. This step creates a pH gradient from one end of the gel to the other, as each particular ampholyte comes to rest at a position coincident with its isoelectric point. At this stage, a solution of proteins is introduced into the gel. The proteins migrate in the electric field until each reaches a point in which the pH resulting from the ampholyte gradient exactly equals its own isoelectric point. Isoelectric focusing thus provides a way of both accurately determining a protein's isoelectric point and effecting separations among proteins whose isoelectric points can differ by as little as a few hundredths of a pH unit.

A popular method for protein molecular weight estimation is called sodium dodecyl sulfate (SDS) gel electrophoresis. This procedure uses the same types of polyacrylamide gels as described previously. The mixture of proteins to be characterized is first completely denatured by the addition of SDS (a detergent) and mercaptoethanol, followed by a brief heating step. The resulting unfolded polypeptide chains have relatively large numbers of SDS molecules bound to them. Because each bound SDS molecule contributes two negative charges, the "native" protein charge is masked by the bound SDS—and thus the net charge of the denatured molecule is proportional to its molecular weight.

An extension of the electrophoretic method combines isoelectric focusing with SDS gel electrophoresis to produce a two-dimensional electrophoretogram. This technique is most valuable for the analysis of very complex protein mixtures. First the sample is run in a one-dimensional pH gradient gel (isoelectric focusing). The resulting narrow strip of gel, containing a partially separated mixture of proteins, is placed alongside a square slab of SDS gel. An electric field is imposed so that the sample moves at a right angle to its motion in the first gel.

Two-dimensional electrophoresis (2-DE) is the highest resolution analytical method for proteins available (S. D. Patterson, "Proteomics: the industrialization of protein chemistry," *Current Opinion in Biotechnology*, Vol. 11, p. 413–418, 2000). The main use of the technology is as a protein profiling expression tool. Complex protein mixtures from paired (or multiple) samples are separated to allow comparison of either their relative abundance using image analysis tools. Another advantage of the method is the ability to extract proteins (or peptides derived from it) from the gel matrix for subsequent identification and/or characterization.

These methods of electrophoresis have several disadvantages. Staining reagent toxicity is one disadvantage of conventional electrophoresis methodologies. For example, ethidium bromide is a powerful mutagen, and is moderately toxic. All solutions containing it must be decontaminated before disposal. Typically, decontamination is performed by diluting solutions with water, mixing with $KMnO_4$, mixing with HCl, and NaOH. While the procedure can reduce the mutagenic activity of ethidium bromide by 3000-fold, the procedure takes several hours and significant residual mutagenic activity has been reported in some cases. In addition, the $KMnO_4$ reagent is itself an irritant and explosive. Thus, the procedure must be carried out carefully by trained staff within a chemical fume hood. Alternative decontamination procedures have been reported, each with various levels of effectiveness, cost, time, and safety.

Another disadvantage of conventional electrophoresis techniques is poor resolution sensitivity. For example, two-dimensional gel electrophoresis can have poor resolution. Out of the entire complement of the genome of about 100,000 genes, a given cell line may express about 10,000 genes—and an even higher number is expressed in tissues. Furthermore, the dynamic range of abundance of proteins in biological samples can be as high as $10^6$. Because even the best two-dimensional gels can routinely resolve no more than 1,000 proteins, only the most abundant proteins can be visualized by gel electrophoresis. (A. Pandey and M. Mann, Nature, Vol. 405, p. 837–846, 2000). Additionally, known methods of electrophoresis modify the separated molecules due to label addition and removal. Other methods require the use of special UV-sensitive film.

Therefore, new electrophoretic techniques that do not use mutagenic materials, that provide high resolution sensitivity, that do not modify the separated molecules, and that do not require specialized film are needed in the art.

SUMMARY OF THE INVENTION

It is an object of the invention to provide methods and compositions for purifying, detecting, separating, and quantifying molecules. This and other objects of the invention are provided by one or more of the embodiments described below.

One embodiment of the invention provides an apparatus comprising a colorimetric resonant label-free optical biosensor and a gel suitable for separation of molecules. The biosensor comprises a one- or two-dimensional grating comprised of a high refractive index material deposited on a substrate comprising a low refractive index material, a film of electrically conducting material on a top surface of the grating, and one or more receptor molecules immobilized on the electrically conducting material. The gel and the colorimetric resonant label-free biosensor are in contact with each other. The calorimetric resonant label-free biosensor can be in or on the gel. The label-free biosensor can be brought into contact with the gel after the molecules have been separated within the gel. The one- or two-dimensional grating can be formed in the substrate material and a film of higher refractive index material can be deposited on the grating. The gel can be selected from the group consisting of an agarose gel, a polyacrylamide gel, a polysaccharide agarose gel, a gradient gel, an isoelectric focusing gel, a sodium dodecyl sulfate (SDS) polyacrylamide gel, a two-dimensional electrophoresis gel, and combinations thereof.

Another embodiment of the invention provides a method of performing gel electrophoresis. The method comprises separating molecules in a gel by electrophoresis, wherein the gel comprises a top surface and a bottom surface, wherein a colorimetric resonant label-free biosensor is in the gel. The biosensor comprises a one- or two-dimensional grating comprised of a high refractive index material deposited on a substrate comprising a low refractive index material, a film of electrically conducting material on a top surface of the grating; and one or more receptor molecules immobilized on the electrically conducting material. A metal sheet is applied to the top surface of the gel, so that the separated molecules are between the metal sheet and the immobilized receptor molecules of the biosensor. Voltage is applied between the metal plate and the biosensor so that the separated molecules move towards the immobilized receptor molecules of the biosensor. Peak wavelength values across the biosensor surface can be determined. Peak wavelength values can be determined by a biosensor illumination and readout system that is located under the biosensor. The illumination and readout system can comprise a dual-fiber optical probe. The illumination and readout system can comprise an imaging spectrometer.

Still another embodiment of the invention provides a method of performing gel electrophoresis. The method comprises separating molecules in a gel by electrophoresis, wherein the gel comprises a top surface and a bottom surface, placing a colorimetric resonant label-free biosensor onto the top surface of the gel. The biosensor comprises a one- or two-dimensional grating comprised of a high refractive index material deposited on a substrate comprising a low refractive index material, a film of electrically conducting material on a top surface of the grating, and one or more receptor molecules immobilized on the electrically conducting material. The one or more receptor molecules are in contact with the top surface of the gel. A voltage is applied to the gel such that the separated molecules are attracted to the immobilized receptor molecules of the biosensor.

The methods and compositions of the invention do not use toxic chemicals such as ethidium bromide. Therefore, there is no requirement to decontaminate and dispose of mutagenic chemical reagents. The instant invention also provides higher sensitivity than current methods used to detect proteins in gels and provides the ability to resolve proteins in 2-DE that are not currently identified because their concentration is too low. Additionally, the present invention results in separated molecules that can recovered in their native state. Finally, the invention provides electrophoresis compositions and methods that do not require the use of specialized films.

BRIEF DESCRIPTION OF THE DRAWINGS

FIG. 1 shows a cross-sectional view of a biosensor.

FIGS. 2A–C shows a linear grating structure (FIG. 2A; top view) used to produce the one-dimensional linear grating guided mode resonant filter "master" structure. First, an 8-inch diameter silicon "master" wafer is produced. The 550 nm period linear grating structure is defined in photoresist using deep-UV photolithography by stepping and repeating the exposure of a 9 mm diameter circular grating reticle over the surface of a photoresist-coated silicon wafer, as shown in FIG. 2B. FIG. 2C shows that the exposure step/repeat procedure produced patterns for two standard format 96-well microtiter plates with 8 rows and 12 columns each.

The exposed photoresist was developed, and the grating structure was permanently transferred to the silicon wafer using a reactive ion etch with a depth of ~200 nm. After etching, the photoresist was removed.

Figure 3A:
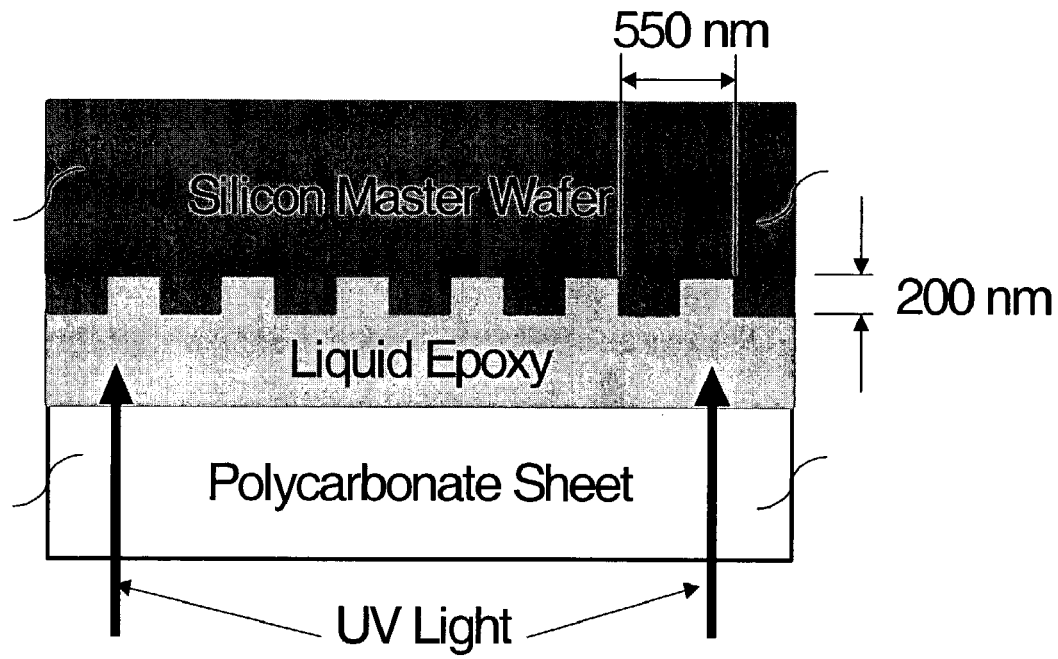
Figure 3B:
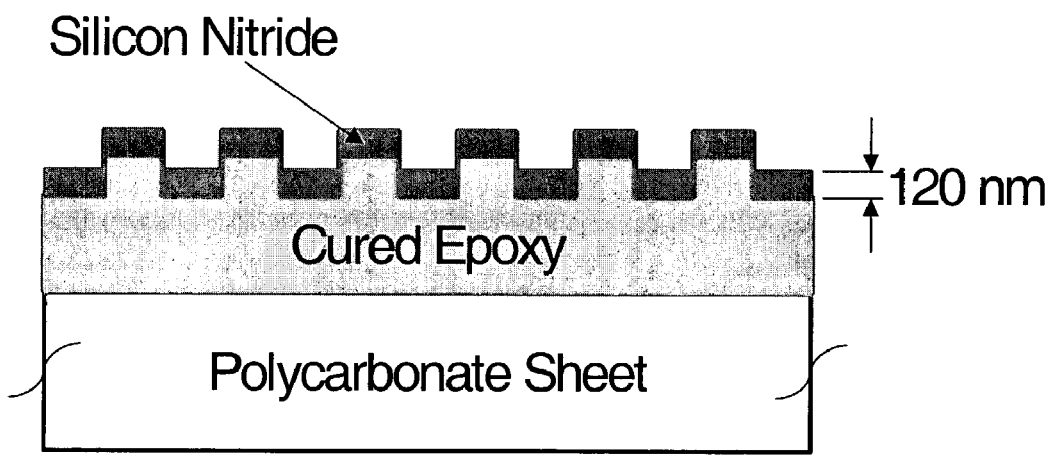

FIGS. 3A–B shows a fabrication process used to produce the biosensor and cross-section of a one-dimensional linear grating sensor. FIG. 3A shows a silicon master wafer used to replicate the biosensor structure into a thin film of epoxy between the silicon and a sheet of plastic film. After the epoxy is cured, the plastic sheet is peeled away. To complete sensor fabrication (FIG. 3B), a thin film of high refractive index dielectric material such as silicon nitride, titanium oxide, tantalum oxide, or zinc sulfide is deposited over the structure.

Figure 4:
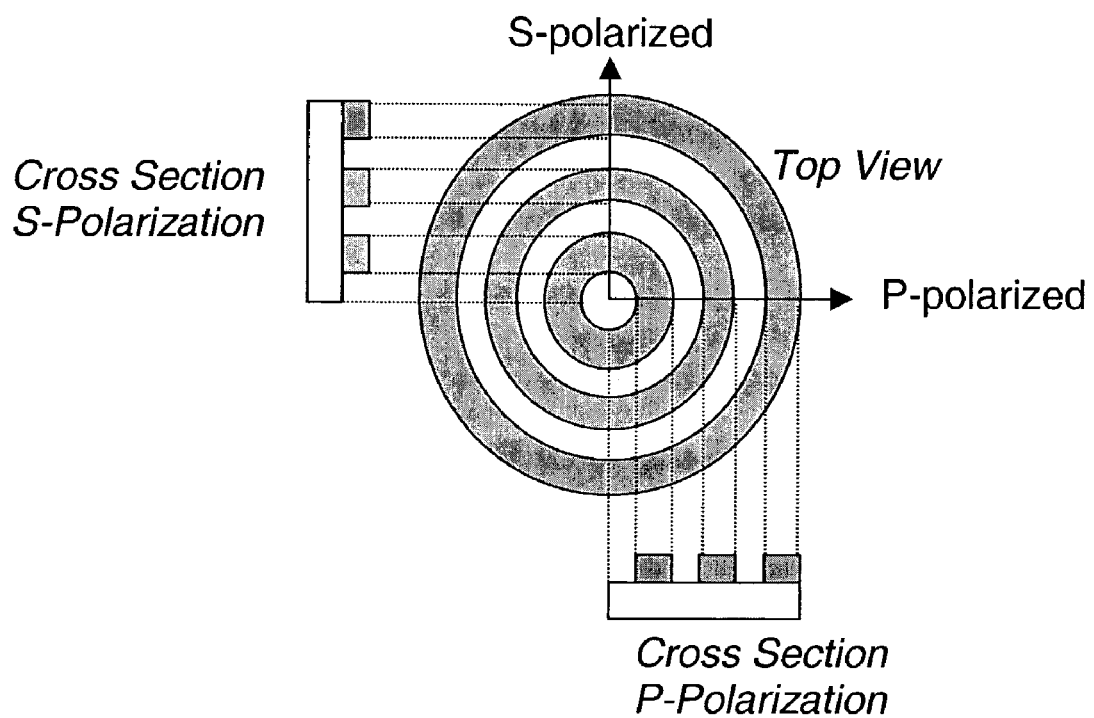

FIG. 4 shows a resonant reflection or structure consisting of a set of concentric rings.

Figure 5:
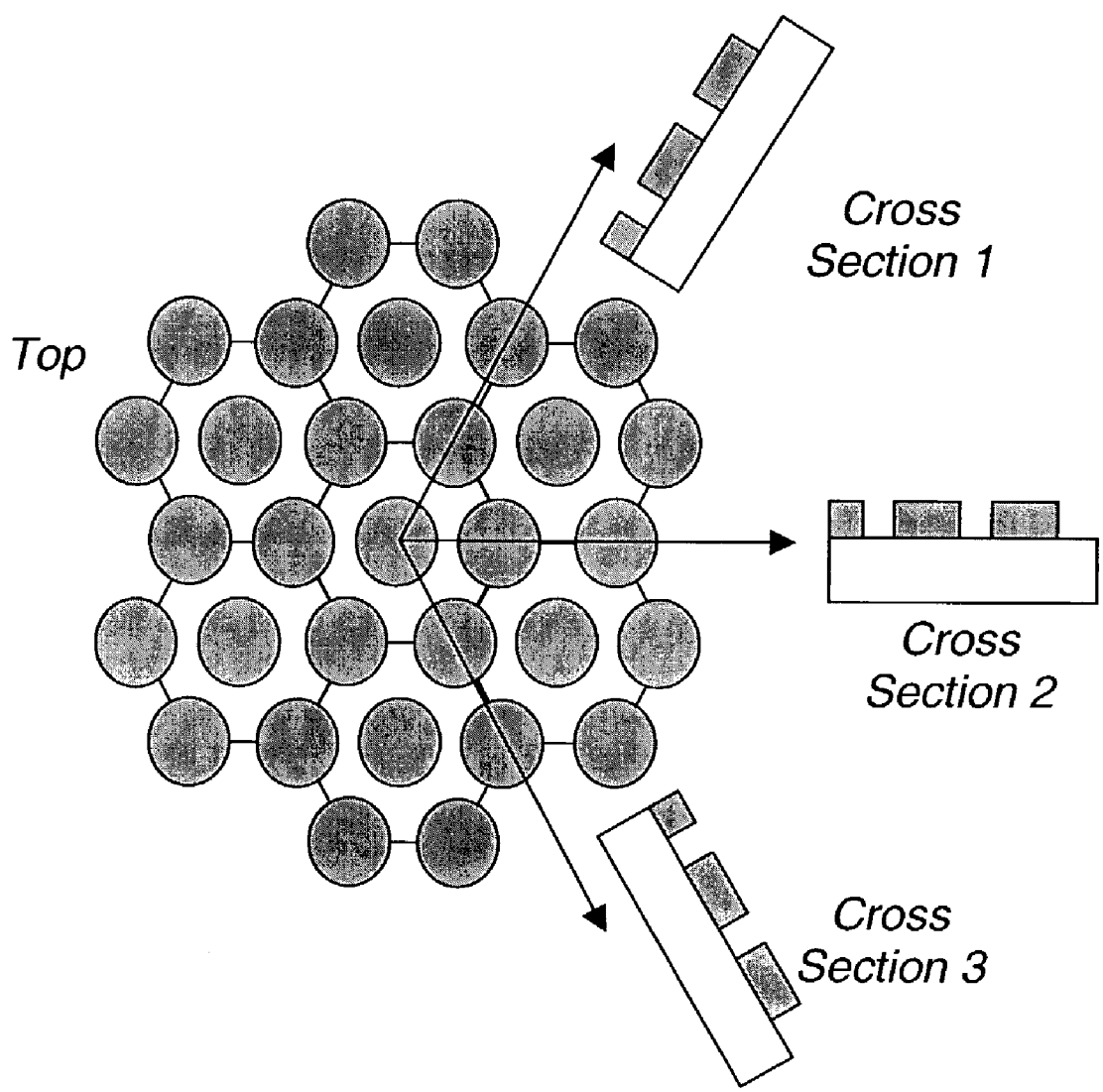

FIG. 5 shows a resonant reflective or transmission filter structure comprising a hexagonal grid of holes (or a hexagonal grid of posts) that closely approximates the concentric circle structure of FIG. 4 without requiring the illumination beam to be centered upon any particular location of the grid.

Figure 6:
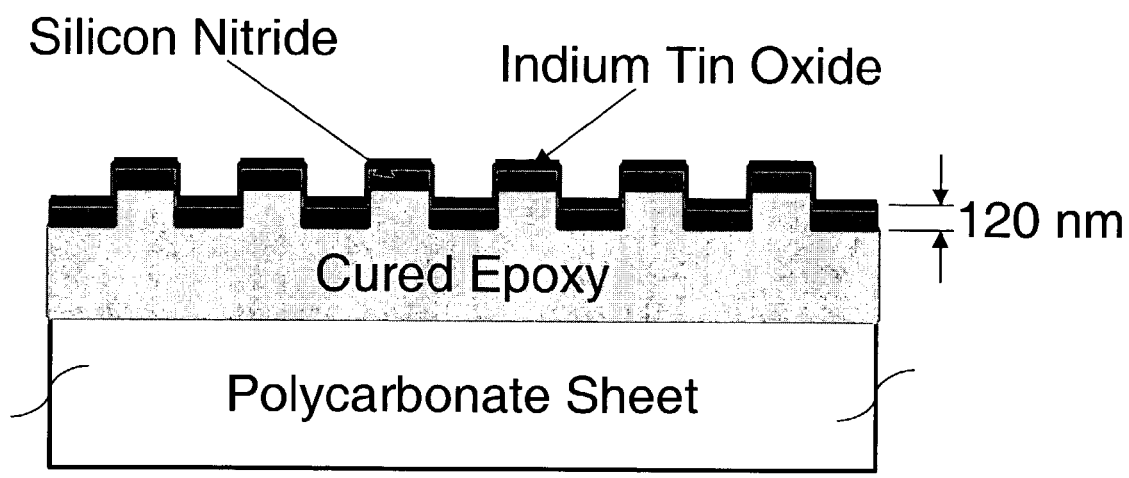

FIG. 6 demonstrates one embodiment of a biosensor of the invention.

Figure 7:
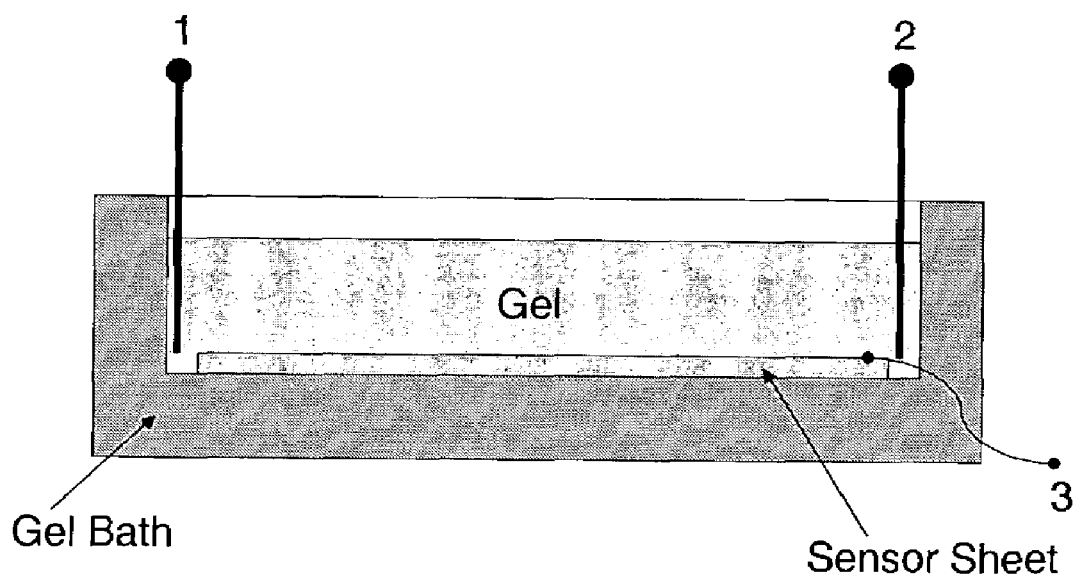

FIG. 7 shows a cross-sectional diagram of one embodiment of the invention comprising an electrophoresis tank with a biosensor sheet placed with the immobilized receptor molecules face-up in the bottom of the tank. The gel is poured over the biosensor sheet, and a test sample is placed at one end of the tank.

Figure 8:
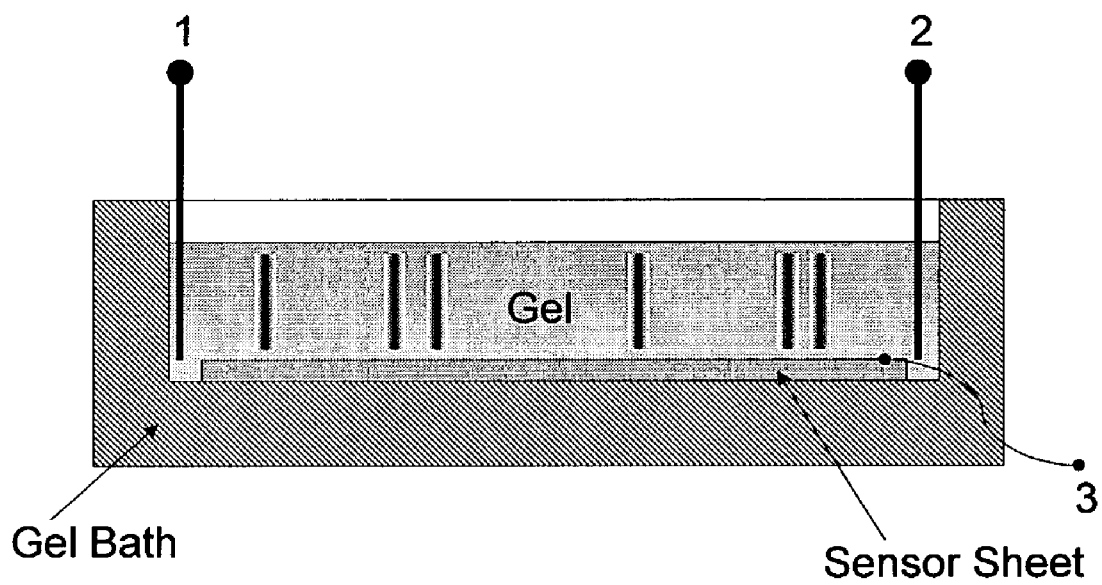

FIG. 8 demonstrates the embodiment shown in FIG. 7 after a voltage has been applied between electrodes 1 & 2 in order to separate nucleic acids or protein molecules along the length of the gel. After the gel separation, the voltage is removed from electrodes 1 & 2.

Figure 9:
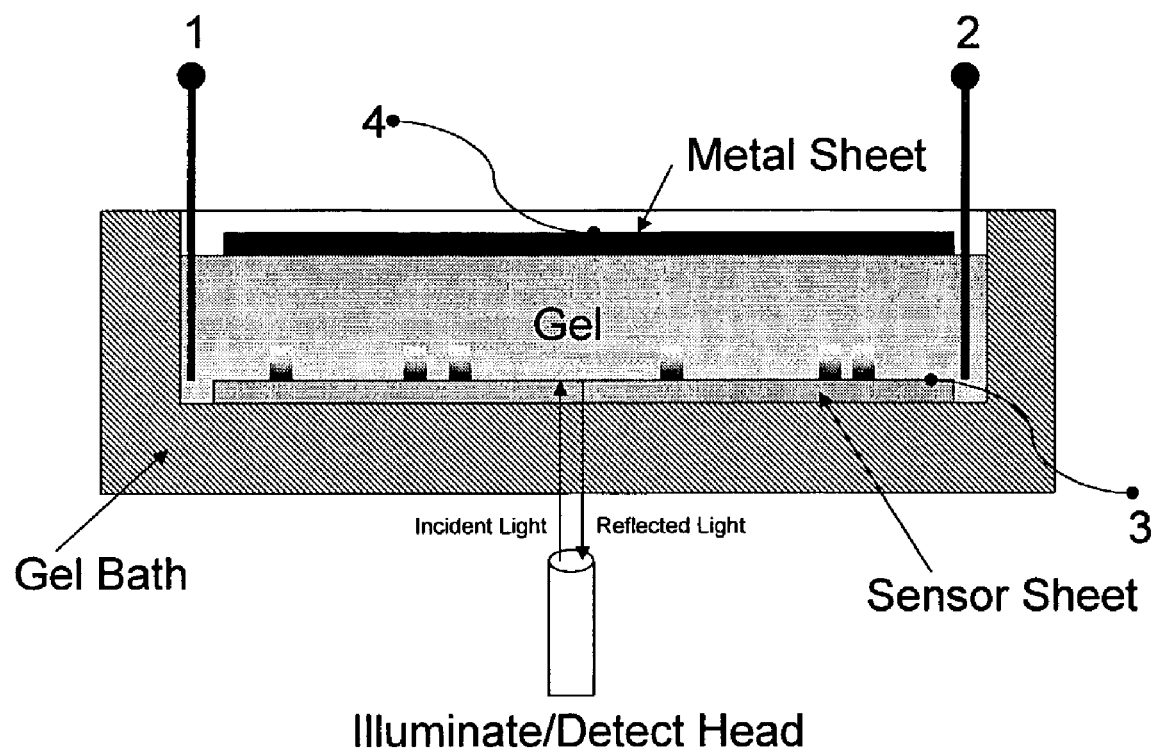

FIG. 9 demonstrates placing a metal plate on the top surface of the gel of FIG. 8, and the connection of the metal plate to electrode 4. A voltage is applied between the biosensor sheet (electrode 3) and the metal plate (electrode 4) in order to draw molecules toward the biosensor surface. FIG. 9 also demonstrates a biosensor illumination and readout system that can be located below a gel tank.

Figure 10:
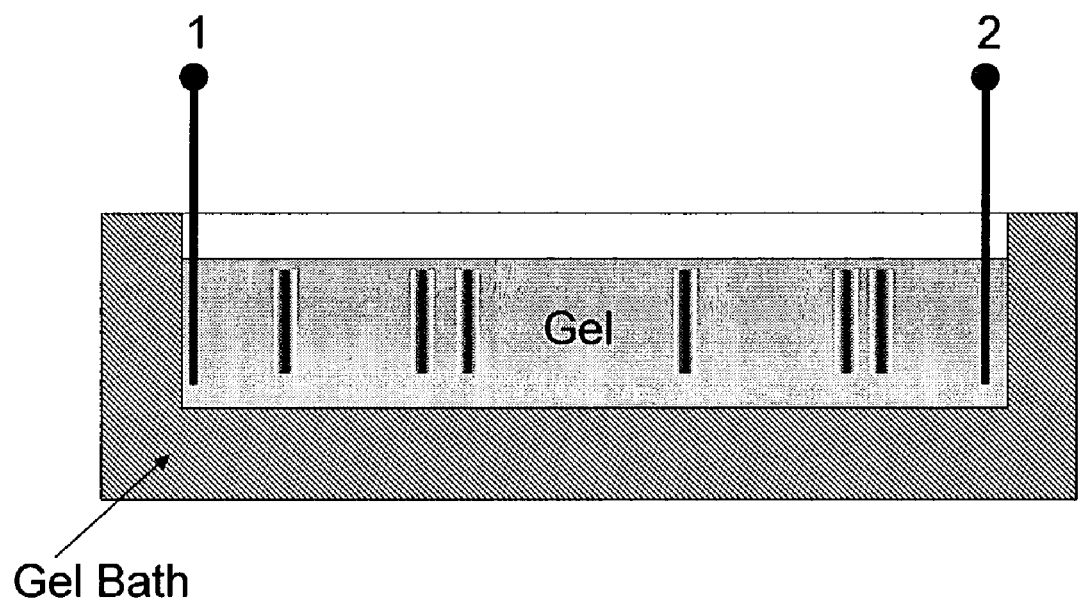

FIG. 10 shows one embodiment of the invention wherein a biosensor will be introduced to the top surface of the gel after performing conventional molecular separation.

Figure 11:
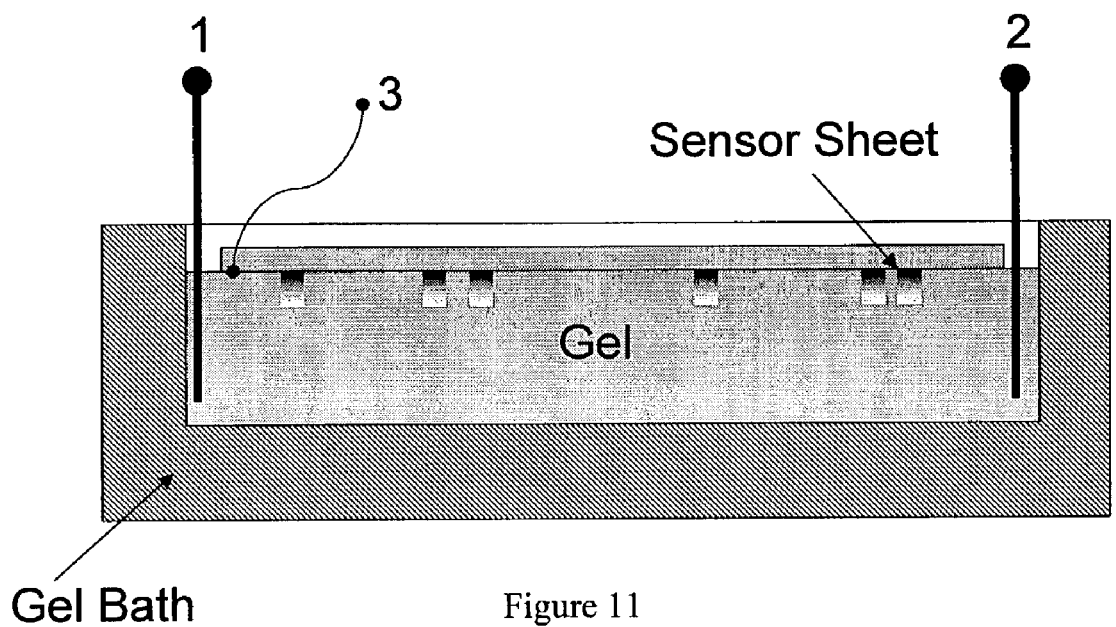

FIG. 11 shows one embodiment of the invention wherein a biosensor sheet with immobilized receptor molecules is placed on top of the gel of FIG. 10 so that the immobilized receptor molecules are in contact with the gel. A voltage is applied to electrode 3 to attract molecules within the gel bands to the biosensor surface. After molecules within the gel have had an opportunity to interact with and bind to the biosensor surface, the biosensor sheet is removed from the gel tank.

Figure 12:
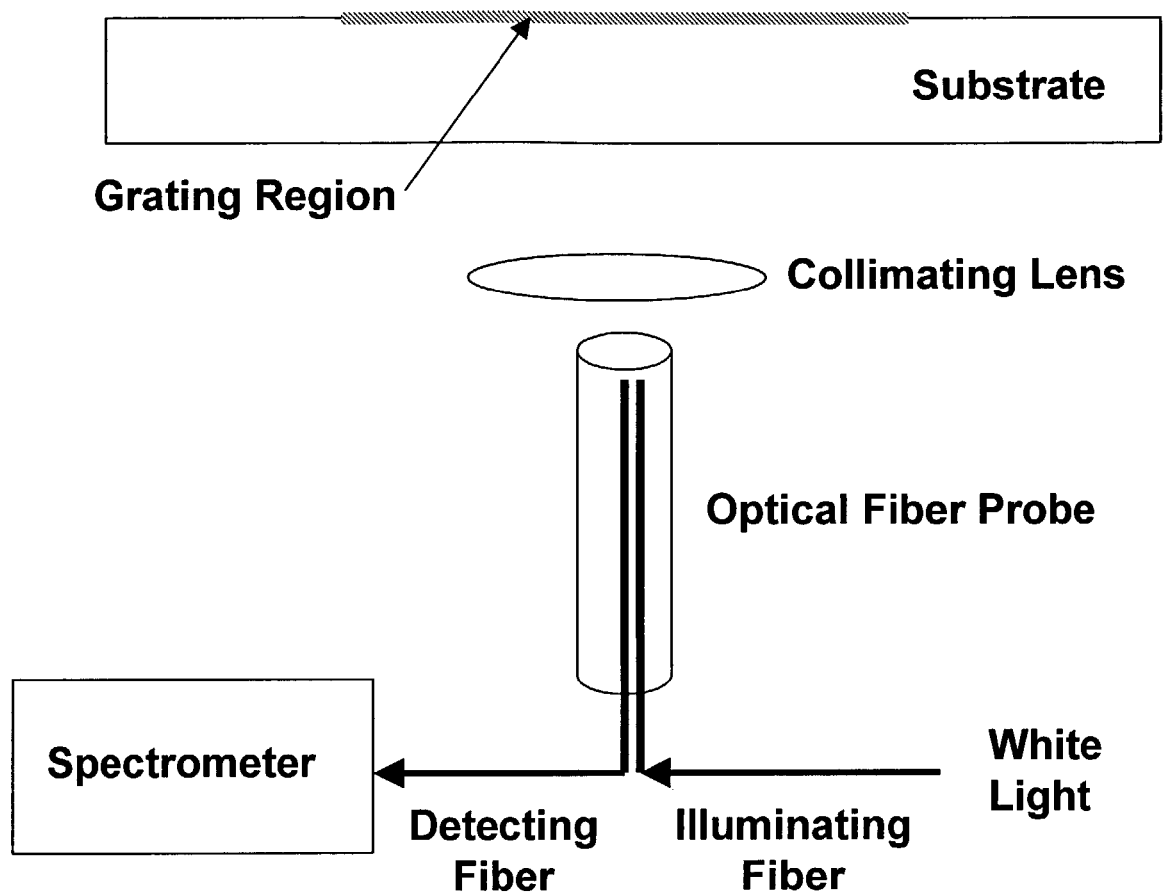

FIG. 12 shows a schematic diagram of one system used to illuminate a biosensor of the invention and to detect the reflected signal.

Figure 13:
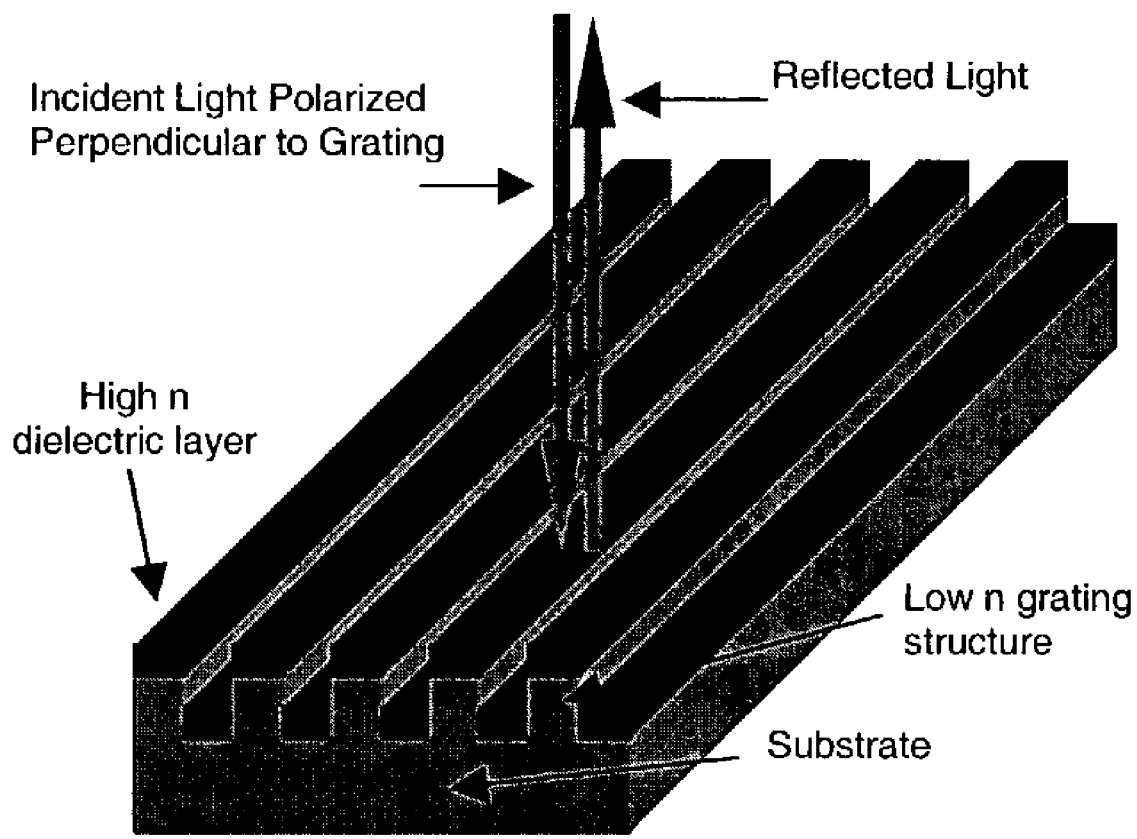

FIG. 13 shows a schematic drawing of a one-dimensional linear grating surface structure.

DETAILED DESCRIPTION OF THE INVENTION

The disclosed invention is an improved system for performing gel electrophoresis. The system incorporates a label-free colorimetric resonant optical biosensor into a gel so that detection of the separated bands of nucleic acids, proteins, or peptides can be performed without the use of colorimetric or fluorescent tags. The use of a biosensor as part of a gel electrophoresis system requires a biosensor that is the same size as a gel plate, and that can produce a digital image of molecular density of molecules within the gel. The biosensor is able to resolve lower molecular concentrations than current gel staining methods.

The use of colorimetric resonant label-free biosensor technologies to enhance the capabilities of gel electrophoresis has been limited by their ability to provide high detection sensitivity and high detection parallelism in a format that is inexpensive to manufacture and package in biosensor areas that are compatible with commonly sized gel plate formats. For example, biosensors fabricated upon semiconductor or glass wafers in batch photolithography/etch/deposition processes are costly to produce and package if the biosensor area is to contain a gel large enough to provide useful molecular resolution. Similarly, the requirement of making electrical connections to individual biosensors in an array poses difficult challenges in terms of package cost and compatibility with exposure of the biosensor to fluids. The instant invention provides a solution to these problems.

Biosensors

Biosensors comprising a narrow bandwidth guided mode resonant filter structure that have been optimized to perform as a biosensor have been described in U.S. application Ser. No. 09/930,352 filed Aug. 15, 2001, corresponding to US01/45455, U.S. application Ser. No. 10/059,060, filed Jan. 28, 2002, and U.S. application Ser. No. 10/058,626, filed Jan. 28, 2002, which are incorporated herein in their entirety.

A calorimetric resonant label-free biosensor comprises a subwavelength structured surface and is used to create a sharp optical resonant reflection at a particular wavelength that can be used to track with high sensitivity the interaction of materials, such as specific binding substances or binding partners or both. A subwavelength structured surface of a biosensor acts as a surface binding platform for specific binding substances.

Unlike optical detection approaches that rely upon interaction of detected molecules with an evanescent wave, the detection phenomenon in these biosensors actually occur within the waveguide, and thus provides for a strong interaction between surface binding events and the transduced signal.

Subwavelength structured surfaces (SWS) are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," Optics Letters, Vol. 21, No. 8, p. 549, April, 1996). A SWS structure contains a surface-relief, one-dimensional or two-dimensional grating in which the grating period is small compared to the wavelength of incident light so that no diffractive orders other than the reflected and transmitted zeroth orders are allowed to propagate. A SWS surface narrowband filter can comprise a one-dimensional or two-dimensional grating supported by a substrate layer and can optionally comprise a cover layer that fills the grating grooves. Preferably, a cover layer comprises a material that has a lower refractive index than a material that comprises the grating. A cover layer can be comprised of, for example, glass (including spin-on glass (SOG)), epoxy, or plastic.

When the effective index of refraction of the grating region is greater than the substrate or the cover layer, a waveguide is created. When a filter is designed properly, incident light passes into the waveguide region and propagates as a leaky mode. A one-dimensional or two-dimensional grating structure selectively couples light at a narrow band of wavelengths into the waveguide. The light propagates only a very short distance (on the order of 10–100 micrometers), undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the one-dimensional or two-dimensional grating are less than the wavelength of the resonant grating effect.

A biosensor, when illuminated with white light, is designed to reflect only a single wavelength or single narrow band of wavelengths. When receptor molecules are attached to the surface of the biosensor, the reflected wavelength (color) is shifted due to the change of the optical path of light that is coupled into the grating. By immobilizing specific binding substances (i.e., receptor molecules) to a biosensor surface, complementary binding partner molecules can be detected without the use of any kind of fluorescent probe or particle label. The detection technique is capable of resolving changes of, for example, ~0.1 nm thickness of protein binding, and can be performed with the biosensor surface either immersed in fluid or dried.

Figure 1:
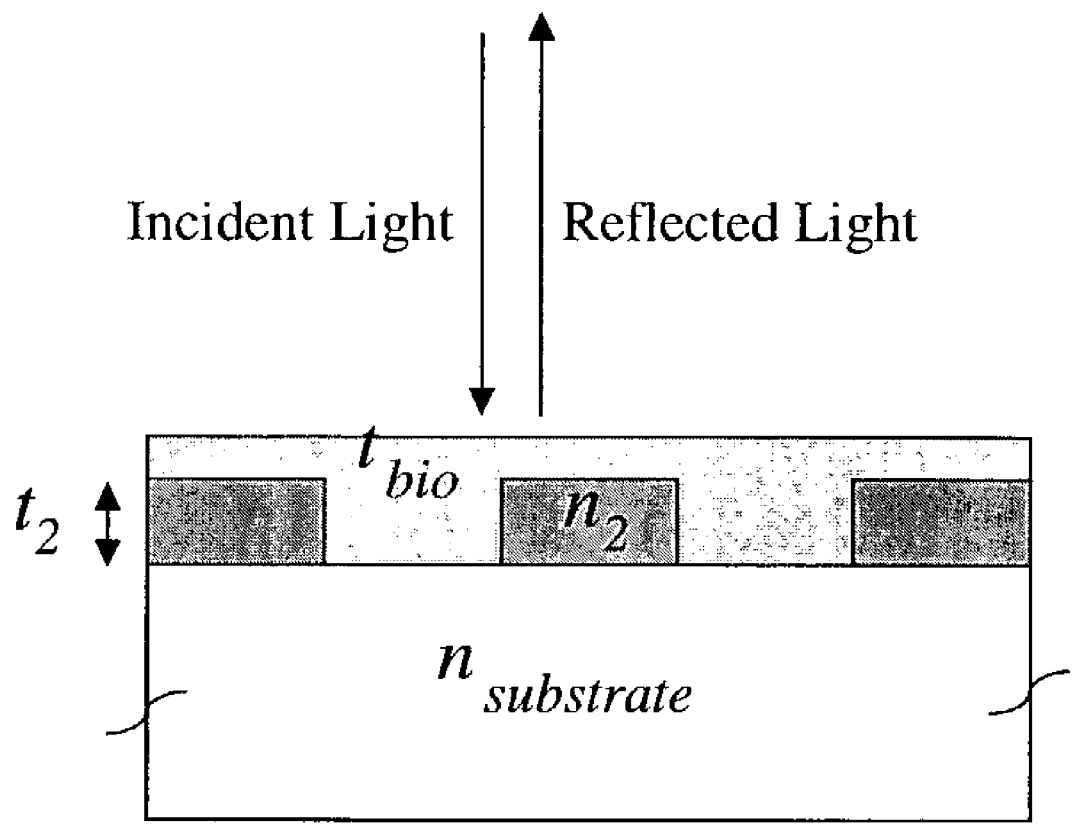
FIG. 1 shows a schematic diagram of one embodiment of an optical grating structure used for a colorimetric resonant reflectance biosensor. $n_{substrate}$ represents substrate material. $n_2$ represents the refractive index of a one- or two-dimensional grating. $n_{bio}$ represents the refractive index of one or more specific binding substances. $t_2$ represents the thickness of the grating. $t_{bio}$ represents the thickness of the layer of one or more specific binding substances.

A schematic diagram of an example of a calorimetric resonant label-free biosensor is shown in FIG. 1. In FIG. 1, $n_{substrate}$ represents a substrate material. $n_2$ represents the refractive index of a grating. $n_{bio}$ represents the refractive index of one or more specific binding substances. $t_2$ represents the thickness of the grating. $t_{bio}$ represents the thickness of the layer of one or more specific binding substances. In one embodiment, are n2>n1. (see FIG. 1). Layer thicknesses (i.e. cover layer, one or more specific binding substances, or a grating) are selected to achieve resonant wavelength sensitivity to additional molecules on the top surface The grating period is selected to achieve resonance at a desired wavelength.

A one-dimensional or two-dimensional grating can be comprised of a material, including, for example, zinc sulfide, titanium dioxide, tantalum oxide, indium tin oxide, and silicon nitride. A cross-sectional profile of the grating can comprise any periodically repeating function, for example, a "square-wave." A grating can be comprised of a repeating pattern of shapes selected from the group consisting of continuous parallel lines, squares, circles, ellipses, triangles, trapezoids, sinusoidal waves, ovals, rectangles, and hexagons. A grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor. In one embodiment of the invention, the depth of the grating is about 0.01 micron to about 1 micron and the period of the grating is about 0.01 micron to about 1 micron.

A colorimetric resonant label-free biosensor can also comprise a one-dimensional linear grating surface structure, i.e., a series of parallel lines or grooves. See e.g., FIG. 2 and FIG. 13. While a two-dimensional grating has features in two lateral directions across the plane of the biosensor surface that are both subwavelength, the cross-section of a one-dimensional grating is only subwavelength in one lateral direction, while the long dimension can be greater than wavelength of the resonant grating effect.

FIG. 3 shows a biosensor cross-sectional profile, in which the one-dimensional grating cross-section is rectangular. Other cross section profiles of the one-dimensional linear grating structure will also produce the guided mode resonance effect. These include, for example, triangular or v-shaped, u-shaped, upside-down v- or u-shapes, sinusoidal, trapezoidal, stepped and square. Any regularly repeating periodic function will provide a guided mode resonant effect. One dimensional linear gratings have resonant characteristics where the illuminating light polarization is oriented perpendicular or parallel to the grating period.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required. A single spectrometer reading can be performed in several milliseconds, thus it is possible to quickly measure a large number of molecular interactions taking place in parallel upon a biosensor surface, and to monitor reaction kinetics in real time.

A one- or two-dimensional grating biosensor can comprise a high refractive index material which is coated as a thin film over a layer of lower refractive index material with the surface structure of a one- or two-dimensional grating. See FIG. 3. Alternatively, a one- or two-dimensional grating biosensor can comprise a low refractive index material substrate, upon which a high refractive index thin film material has been patterned into the surface structure of a one- or two-dimensional grating. The low refractive index material can be glass, plastic, polymer, or cured epoxy. The high refractive index material must have a refractive index that is greater than the low refractive index material.

A one- or two-dimensional linear grating biosensor surface contains an optical structure that, when illuminated with collimated white light, is designed to reflect only a narrow band of wavelengths. The narrow wavelength band is described as a wavelength "peak." The "peak wavelength value" (PWV) changes when biological or other material is deposited or removed from the biosensor surface. A readout instrument illuminates distinct locations on the biosensor surface with collimated white light, and collects collimated reflected light. The collected light is gathered into a wavelength spectrometer for determination of PWV.

A one-dimensional linear grating has the same pitch (i.e. distance between regions of high and low refractive index), period, layer thicknesses, and material properties as a two-dimensional grating. However, light must be polarized perpendicular or parallel to the grating lines in order to be resonantly coupled into the optical structure. Therefore, a polarizing filter oriented with its polarization axis perpendicular or parallel to the one-dimensional linear grating must be inserted between the illumination source and the biosensor surface. Because only a small portion of the illuminating light source is correctly polarized, a longer integration time is required to collect an equivalent amount of resonantly reflected light compared to a two-dimensional grating.

In general, a biosensor of the invention will be illuminated with white light that will contain light of every polarization angle. The orientation of the polarization angle with respect to repeating features in a biosensor grating will determine the resonance wavelength. For example, a one-dimensional linear grating biosensor structure consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor structure can generally be designed to optimize the properties of only one polarization (generally the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron. FIG. 4

In another embodiment, an array of holes or posts are arranged to closely approximate the concentric circle structure described above without requiring the illumination beam to be centered upon any particular location of the grid. See e.g. FIG. 5. Such an array pattern is automatically generated by the optical interference of three laser beams incident on a surface from three directions at equal angles. In this pattern, the holes (or posts) are centered upon the corners of an array of closely packed hexagons as shown in FIG. 5. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A biosensor component of the invention comprises a label-free resonant biosensor, as described above, and further comprises a thin film of electrically conducting material over the high refractive index material. Specific binding substances are immobilized to the top surface of the thin film of electrically conducting material. This biosensor is called an electrophoresis adapted biosensor.

One embodiment of an electrophoresis adapted biosensor is shown in FIG. 6. The polycarbonate sheet is used during fabrication of the biosensor and is removed prior to use of the biosensor. The biosensor structure requires a material that is electrically conducting and that does not absorb wavelengths near the resonant wavelength. An indium tin oxide (ITO) layer of about 3 nm to about 5 nm thickness provide the desired properties. An electrode is connected to the ITO thin film so that an electrical potential can be applied in common to the entire biosensor sheet. A receptor molecule that, for example, will nonspecifically bind all proteins or nucleic acids within the gel is immobilized onto the electrically conducting material of the biosensor sheet. The immobilization process can comprise two steps: First, a biosensor can be "activated" with surface functional groups. Second, the receptor molecules can be immobilized on the activated surface. The receptor molecule can be, for example, a bifunctional linker molecule that covalently attaches to the activated surface at one end, and presents a binding moiety for the detected molecules at the other end.

Fabrication

Techniques for making two-dimensional gratings are disclosed in Wang, J. Opt. Soc. Am No. 8, August 1990, pp. 1529–44. However, an important aspect of the current invention is the ability to produce sheets of plastic film that contain the biosensor structure. Rather than perform sub-micron definition of grating features using photolithography on the biosensor itself, a "master" wafer is created in silicon that is used as a template for producing the biosensor structure on plastic by a high-definition microreplication process. The use of a continuous plastic roll for the biosensor substrate enables other processes, such as dielectric thin film coating and surface activation, to be performed in a substantially more efficient manner. Most importantly, the ability to produce a high-sensitivity biosensor in plastic over large surface areas enables incorporation of the biosensor into large area disposable assay formats such as microtiter plates and microarray slides. See, e.g., U.S. application Ser. No. 10/058,626, entitled "Optical Detection of Label-Free Biomolecular Interactions Using Microreplicated Plastic Sensor Elements" filed Jan. 28, 2002

Receptor Molecules

One or more specific binding substances, i.e., receptor molecules, can be immobilized on the surface of a biosensor by for example, physical adsorption or by chemical binding. A specific binding substance can be, for example, a nucleic acid, polypeptide, antigen, polyclonal antibody, monoclonal antibody, single chain antibody (scFv), F(ab) fragment, $F(ab')_2$ fragment, Fv fragment, small organic molecule, cell, virus, bacteria, polymer, peptide solutions, single- or double-stranded DNA solutions, RNA solutions, solutions containing compounds from a combinatorial chemical library, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatite fluid.

The one or more specific binding substances can be arranged in a microarray of distinct locations on a biosensor. A microarray of specific binding substances comprises one or more specific binding substances on a surface of a biosensor of the invention such that a surface contains many distinct locations, each with a different specific binding substance or with a different amount of a specific binding substance. For example, an array can comprise 1, 10, 100, 1,000, 10,000, or 100,000 distinct locations. Such a biosensor surface is called a microarray because one or more specific binding substances are typically laid out in a regular grid pattern in x-y coordinates. However, a microarray of the invention can comprise one or more specific binding substance laid out in any type of regular or irregular pattern. For example, distinct locations can define a microarray of spots of one or more specific binding substances. A microarray spot can be about 50 to about 500 microns in diameter. A microarray spot can also be about 150 to about 200 microns in diameter. One or more specific binding substances can be bound to their specific binding partners.

A specific binding substance specifically binds to a binding partner that is brought into contact with the surface of a biosensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, polymer, peptide solutions, single- or double-stranded DNA solutions, RNA solutions, solutions containing compounds from a combinatorial chemical library and biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatitc fluid.

In one embodiment of the invention an electrophoresis adapted biosensor has specific binding substances immobilized to it that will bind any type of nucleic acid, protein or other binding partner applied to the biosensor.

Immobilization of Receptor Molecules

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass, plastic and epoxy for use in various types of microarrays and biosensors. These same methods can be readily adapted to a biosensor of the invention.

Gels

An electrophoresis adapted biosensor can be incorporated or used with any type of gel separation device used to separate nucleic acids, proteins, or peptides. Gel separation devices include, for example, agarose gels, polyacrylamide gels, polysaccharide agarose gels, gradient gels, isoelectric focusing gels, SDS polyacrylamide gels, two-dimensional electrophoresis gels, or combinations thereof.

Methods of Separation, Purification, Detection, and Quantification

An electrophoresis adapted biosensor comprising a film of electrically conducting material can occur within a gel. In this embodiment, an electrophoresis adapted biosensor is added to the gel before separation of molecules within the gel occurs. For example, FIG. 7 shows a cross sectional diagram of an electrophoresis tank with a biosensor placed face-up, i.e., receptor molecule side up, in the bottom of the tank. A gel is poured over the biosensor, and a test sample is placed at one end of the tank. A voltage is applied between electrodes 1 and 2 in order to separate nucleic acids or protein molecules along the length of the gel, as shown in FIG. 8. After the gel separation, the voltage is removed from electrodes 1 and 2. A metal plate is placed on the top surface of the gel and connected to electrode 4 as shown in FIG. 9. A voltage is applied between the biosensor (electrode 3) and the metal plate (electrode 4) in order to draw molecules toward the biosensor surface. Because the gel is much thinner than its length, application of a voltage of, for example, less than 5 V for less than 5 minutes will concentrate the separated gel bands at the biosensor surface. If the biosensor surface contains an immobilized receptor molecule that can nonselectively bind all molecules in the gel bands, the optical density at the biosensor surface within the gel band regions will be higher than regions without a gel band. The peak wavelength value (PWV) of the biosensor will be higher in the regions of high surface optical density compared to the regions of lower surface optical density. A PWV image of the biosensor can be scanned before and after the attachment process to provide an image of PWV shift. The PWV-shift image is obtained immediately after performing gel separation—without performing additional chemical labeling steps. The PWV-shift image is automatically digitized. Therefore, no film exposure, image development, image scanning, or image registration is required to transfer gel band position data into an electronic format.

Alternatively, a biosensor is introduced to the top surface of the gel after performing conventional molecular separation, as shown, for example, in FIG. 10. In this case, a biosensor is placed on top of the gel so that the immobilized receptor molecules are in contact with the gel, and a voltage is applied to electrode 3 (FIG. 11) to attract molecules within the gel bands to the biosensor surface. After molecules within the gel have had an opportunity to interact with and bind to the biosensor surface, the biosensor is removed from the gel. The biosensor can be rinsed to remove unwanted material, dried if desired, and placed within a separate PWV imaging system. In this method, the PWV imaging system does not need to be integrated with the gel tank. The PWV-shift image is automatically digitized. Therefore, no film exposure, image development, image scanning, or image registration is required to transfer gel band position data into an electronic format.

Therefore, a biosensor of the invention can be used to detect, quantify, separate, and purify molecules. Molecules in their native state can be removed from the surface of a biosensor in their native state for further analysis or use.

Detection

PWV Image Scanner Instrument

A schematic diagram of an example of a system used to illuminate a biosensor and to detect a reflected signal is shown in FIG. 12. In order to detect a reflected resonance, a white light source illuminates a ~1 mm diameter region of the grating surface through, for example, a 100 micrometer diameter fiber optic and a collimating lens at nominally normal incidence through the bottom of a biosensor. A detection fiber is bundled with the illumination fiber for gathering reflected light for analysis with a spectrometer (Ocean Optics). A biosensor sits upon a motion stage so that each column can be addressed in sequence.

As shown in FIG. 9, a biosensor illumination and readout system can be located below a gel tank. The purpose of the illumination/readout system is to measure the PWV across all regions of the biosensor sheet, and to construct a "PWV image." The PWV image is a plot of the biosensor PWV value as a function of its location in x-y coordinates within the biosensor. In one embodiment, the illumination/readout system consists of a dual-fiber optical probe. One fiber within the probe casts a small spot of collimated white light onto the biosensor surface, while the second fiber collects light that is reflected from the biosensor surface. The probe is scanned over the biosensor surface in small increments so the PWV is measured in all locations on the biosensor surface. Alternatively, a larger region of the biosensor surface can be illuminated with collimated white light, and an imaging spectrometer may measure the PWV as a function of position within the illuminated area.

The following are provided for exemplification purposes only and are not intended to limit the scope of the invention described in broad terms above. All references cited in this disclosure are incorporated herein by reference.

EXAMPLES

Example 1

Biosensor Design and Fabrication

A biosensor structure requires a grating with a period lower than the wavelength of the resonantly reflected light. As shown in FIG. 6, a grating structure can be fabricated from a low refractive index material that is overcoated with a thin film of higher refractive index material. Such a grating structure was microreplicated within a layer of cured epoxy, as described below.

First, an 8-inch diameter silicon "master" wafer was produced. The 550 nm period linear grating structure was defined in photoresist using deep-UV photolithography by stepping and repeating the exposure of a 9 mm diameter circular grating reticle over the surface of a photoresist-coated silicon wafer. The exposure step/repeat procedure produced patterns for two standard format 96-well microtiter plates with 8 rows and 12 columns each. The exposed photoresist was developed, and the grating structure was permanently transferred to the silicon wafer using a reactive ion etch with a depth of 200 nm. After etching, the photoresist was removed.

The grating structure was replicated onto a 0.005 inch thick sheet of polycarbonate by distributing a thin layer of epoxy between the silicon master wafer and a section of the polycarbonate sheet. The liquid epoxy conforms to the shape of the master grating, and is subsequently cured by exposure to ultraviolet light. The cured epoxy preferentially adheres to the polycarbonate sheet, and is peeled away from the silicon wafer. Biosensor fabrication was completed by sputter deposition of 120 nm silicon nitride on the cured epoxy grating surface. Following silicon nitride deposition, 3×5-inch microtiter plate sections were cut from the biosensor sheet, activated with amine functional groups (using the protocol defined below) and attached to the bottoms of bottomless 96-well microtiter plates (Costar and Greiner) with epoxy.

Surface Activation and Attachment of Receptor Molecule

After silicon nitride deposition, the biosensors were activated with amine functional groups to enable various bifunctional linker molecules to be attached to the surface in a known orientation. Amine activation was performed by immersion of the biosensor in 10% 3-aminopropyltriethoxysilane (Pierce) solution in ethanol for 1 min, followed by a brief ethanol rinse. Activated biosensors were then dried at 70° C. for 10 min.

A simple, colorimetric method was used to determine the density of amine groups on the surface. The amine-activated biosensor was immersed in 0.1 mM of sulfosuccinimidyl-4-O-(4,4'-dimethoxytrityl)-butyrate (s-SDTB, Pierce), solution made in 50 mM sodium bicarbonate (pH 8.5), and shaken vigorously for 30 minutes. The biosensor was then washed with deionized water and subsequently treated with 30% perchloric acid (Sigma). The solution turned orange when the biosensor was amine-activated and remained colorless when the biosensor was not amine-activated. This method indicated that the surface density of the amine groups is $\sim 2 \times 10^{14}$ groups/cm$^2$.

The purpose of this work is to demonstrate the use of a plastic biosensor for the detection of a well-characterized protein—protein binding interaction. The protein—protein system selected for this study was detection of anti-biotin IgG antibody using biotin immobilized on the biosensor surface as a receptor molecule. Therefore, a protocol for immobilization of biotin on the biosensor surface was developed that utilizes a bifunctional NHS-PEG linker molecule to act as an intermediary between the amine surface group and the biotin. The NHS-PEG molecule is designed specifically to enable NHS to preferentially bind to the amine-activated surface, leaving the PEG portion of the molecule oriented away from the surface. The NHS-PEG linker molecule serves to separate the biotin molecule from the biosensor surface by a short distance so it may retain its conformation, and thus its affinity for other molecules. The PEG also serves to prevent nonspecific binding of proteins to the biosensor.

After attachment of an amine-activated biosensor into the bottom of microtiter plates, individual microtiter wells were prepared with three different surface functional groups in order to provide sufficient experimental controls for the detection of anti-biotin IgG. First, amine-activated surfaces are studied without additional modification. The amine-activated surface is expected to bind proteins nonspecifically, but not with high affinity. Second, microtiter wells with the NHS-PEG bifunctional linker molecule were prepared. The NHS-PEG molecule is expected to provide a surface that does not bind protein. Third, microtiter wells with an NHS-PEG-Biotin linker molecule were prepared. The NHS-PEG-Biotin molecule is expected to bind strongly to anti-biotin IgG.

To activate an amine-coated biosensor with biotin, 2 ml of NHS-PEG-Biotin (Shearwater) solution in TPBS (a reference buffer solution of 0.01% Tween 20™ in phosphate buffer solution, pH 8) at 1.0 mg/ml concentration was added to the biosensor surface, and incubated at 37° C. for 1 hour. An identical procedure was used for attachment of the NHS-PEG (Shearwater) molecule without biotin.

PWV Image Scanner Instrument

A schematic diagram of the system used to illuminate the biosensor and to detect the reflected signal is shown in FIG. 12. In order to detect the reflected resonance, a white light source illuminates a ~1 mm diameter region of the grating surface through a 100 micrometer diameter fiber optic and a collimating lens at nominally normal incidence through the bottom of the biosensor sheet. A detection fiber is bundled with the illumination fiber for gathering reflected light for analysis with a spectrometer (Ocean Optics). The biosensor sheet sits upon a motion stage so that each column can be addressed in sequence.

I claim:

1. A method of performing gel electrophoresis comprising:
   (a) separating molecules in a gel by electrophoresis, wherein the gel comprises a top surface and a bottom surface, wherein a calorimetric resonant label-free biosensor is in the gel, wherein the biosensor comprises:
      (i) a one- or two-dimensional grating comprised of a high refractive index material deposited on a substrate comprising a low refractive index material;
      (ii) a film of electrically conducting material on a top surface of the grating; and
      (iii) one or more receptor molecules immobilized on the electrically conducting material;
   (b) applying a metal sheet to the top surface of the gel, so that the separated molecules are between the metal sheet and the immobilized receptor molecules of the biosensor; and (c) applying voltage between the metal plate and the biosensor so that the separated molecules move towards the immobilized receptor molecules of the biosensor.

2. The method of claim 1, further comprising determining peak wavelength values across the biosensor surface.

3. The method of claim 2, wherein the peak wavelength values are determined by a biosensor illumination and readout system that is located under the biosensor.

4. The method of claim 3, wherein the illumination and readout system comprises a dual-fiber optical probe.

5. The method of claim 3, wherein the illumination and readout system comprises an imaging spectrometer.

6. The method of claim 1, wherein the one- or two-dimensional grating is formed in the substrate material and a film of higher refractive index material is deposited on a top surface of the grating.

7. The method of claim 1, wherein the gel is selected from the group consisting of an agarose gel, a polyacrylamide gel, a polysaccharide agarose gel, a gradient gel, an isoelectric focusing gel, a sodium dodecyl sulfate (SDS) polyacrylamide gel, a two-dimensional electrophoresis gel, and combinations thereof.

8. A method of performing gel electrophoresis comprising:
(a) separating molecules in a gel by electrophoresis, wherein the gel comprises a top surface and a bottom surface,
(b) placing a colorimetric resonant label-free biosensor onto the top surface of the gel, wherein the biosensor comprises:
(i) a one- or two-dimensional grating comprised of a high refractive index material deposited on a substrate comprising a low refractive index material;
(ii) a film of electrically conducting material on a top surface of the grating; and
a. one or more receptor molecules immobilized on the electrically conducting material;
wherein, the one or more receptor molecules are in contact with the top surface of the gel;
(c) applying a voltage to the gel such that the separated molecules are attracted to the immobilized receptor molecules of the biosensor.

9. The method of claim 8, further comprising determining peak wavelength values across the biosensor surface.

10. The method of claim 9, wherein the peak wavelength values are determined by a biosensor illumination and readout system that is located under the biosensor.

11. The method of claim 10, wherein the illumination and readout system comprises a dual-fiber optical probe.

12. The method of claim 10, wherein the illumination and readout system comprises an imaging spectrometer.

13. The method of claim 8, wherein the one- or two-dimensional grating is formed in the substrate material and a film of higher refractive index material is deposited on a top surface of the grating.

14. The method of claim 8, wherein the gel is selected from the group consisting of an agarose gel, a polyacrylamide gel, a polysaccharide agarose gel, a gradient gel, an isoelectric focusing gel, a sodium dodecyl sulfate (SDS) polyacrylamide gel, a two-dimensional electrophoresis gel, and combinations thereof.

* * * * *

UNITED STATES PATENT AND TRADEMARK OFFICE
CERTIFICATE OF CORRECTION

PATENT NO. : 7,074,311 B1
APPLICATION NO. : 10/431948
DATED : July 11, 2006
INVENTOR(S) : Cunningham It is certified that error appears in the above-identified patent and that said Letters Patent is hereby corrected as shown below:

Col. 3, Line 51, "calorimetric" should read --colorimetric--.

Col. 6, Line 33, "calorimetric" should read --colorimetric--.

Col. 7, Line 30, "calorimetric" should read --colorimetric--.

Col. 14, Line 55, "calorimetric" should read --colorimetric--.

Signed and Sealed this

Twenty-third Day of September, 2008

JON W. DUDAS
*Director of the United States Patent and Trademark Office*